United States Patent [19]

Hilliard

[11] Patent Number: 4,836,014

[45] Date of Patent: Jun. 6, 1989

[54] SIMULATED IN VIVO MEASUREMENT OF SKIN CHARACTERISTICS

[75] Inventor: Peter Hilliard, Bethel, Conn.

[73] Assignee: Clairol Incorporated, New York, N.Y.

[21] Appl. No.: 171,594

[22] Filed: Mar. 22, 1988

[51] Int. Cl.$^4$ .............................................. G01N 5/04
[52] U.S. Cl. ...................................................... 73/76
[58] Field of Search ......................... 73/75, 76, 73, 579

[56] References Cited

U.S. PATENT DOCUMENTS

| | | | |
|---|---|---|---|
| 4,050,995 | 9/1977 | Bredeweg | 73/76 X |
| 4,297,884 | 11/1981 | Leveque et al. | 73/579 |
| 4,682,608 | 7/1987 | DeRigal et al. | 73/579 X |
| 4,711,244 | 12/1987 | Kuzara | 73/73 X |

Primary Examiner—Stewart J. Levy
Assistant Examiner—Joseph W. Roskos
Attorney, Agent, or Firm—Gene Warzecha

[57] ABSTRACT

A method and apparatus for conducting various experiments on skin samples under simulated in vivo conditions. The apparatus includes, in one embodiment, a platform for supporting the skin sample over a chamber containing liquid at a controlled temperature. An activating probe is attached to the surface of the skin sample and is activated in a predetermined manner. The probe is also used to measure the resulting deformations of the skin sample to determine the visco-elastic properties of the skin under various temperature and humidity conditions. The apparatus also includes an access part for applying selected topical solutions to the skin sample. In another embodiment, the apparatus includes additional elements for enclosing the air space above a skin sample and for measuring the transepidermal water loss through the sample.

13 Claims, 3 Drawing Sheets

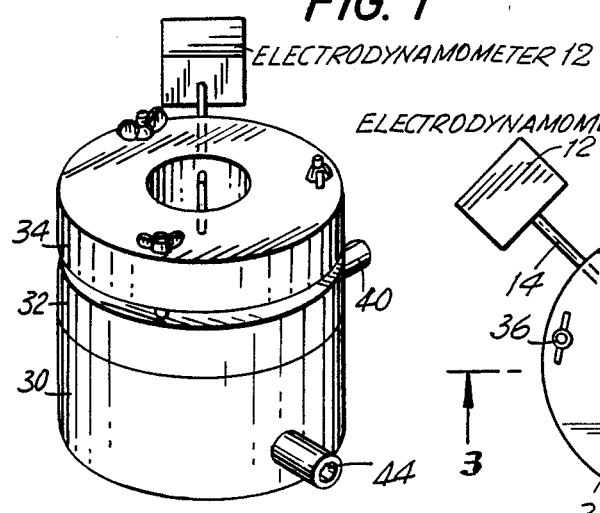
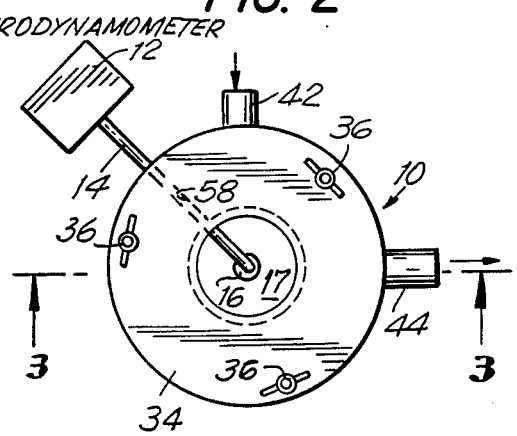
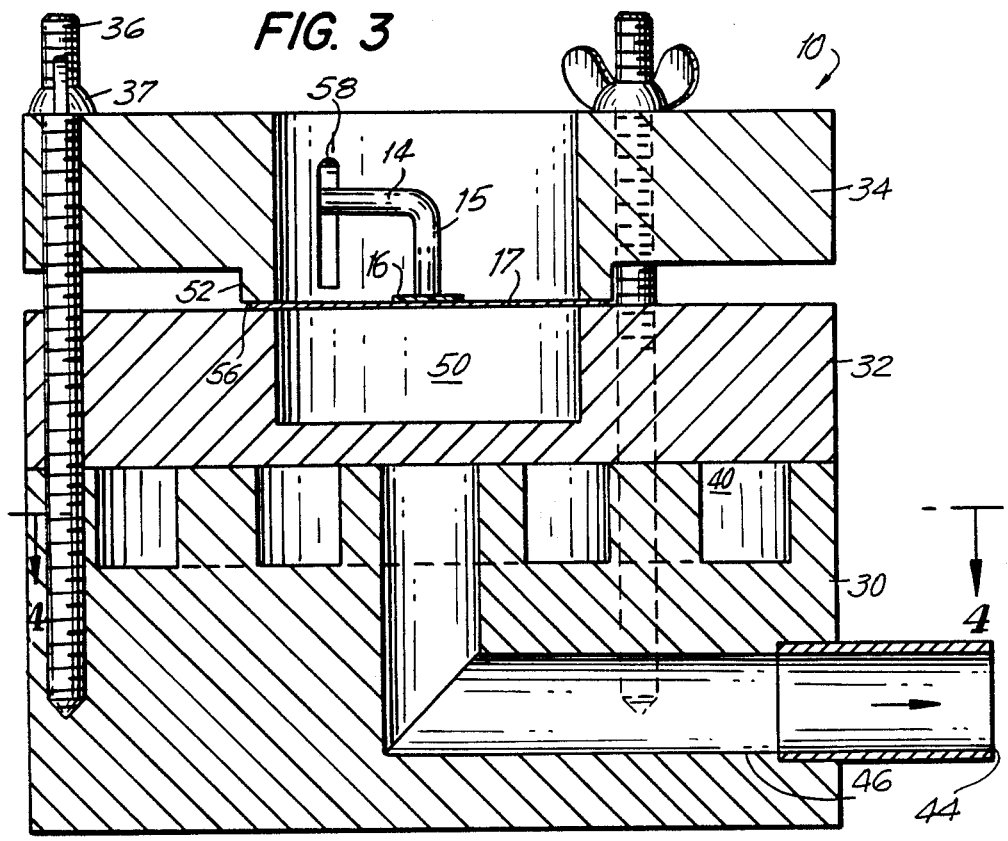

SIMULATED IN VIVO MEASUREMENT OF SKIN CHARACTERISTICS

BACKGROUND OF THE INVENTION

1. Field of the Invention

This invention relates to a method and apparatus for determining various properties of skin. More particularly, the invention relates to an in vitro method and apparatus for determining the viscoelastic properties and other characteristics of skin under various conditions.

2. Description of the Prior Art

In the course of determining the proper treatment of various skin conditions, it has been found necessary to evaluate the effects on the stratum corneum induced by various topically applied agents or other treatments. It is known that the various physical properties of the stratum corneum are related to its composition and macromolecular structure which are affected by its state of hydration or disease condition. Various techniques are known to measure the viscoelastic and dimensional properties of the stratum corneum and determine the changes in these properties which result under various conditions. These techniques include both in vivo measurements of various portions of the skin of living subjects and in vitro measurements of excised skin samples.

The usefulness of data derived from in vivo measurements is limited in view of the difficulty in making accurate measurements on living subjects. The measurement of viscoelastic properties requires extremely sensitive instrumentation capable of detecting small skin displacements. Because of the requisite sensitivity, this instrumentation also detects extraneous vibrations inherent in the use of living subjects and produces measurents having a relatively high experimental error. Furthermore, in vivo measurements are limited in their usefulness because of the inability to vary the ambient conditions to which the living subject may be exposed during the measurement process.

In vitro measurements of the viscoelastic properties of skin are somewhat more accurate since certain ambient conditions may be varied in a controlled manner and since the extraneous vibrations or other variations inherently introduced by living subjects may be essentially eliminated. One type of vitro technique is thermomechanical analysis (TMA) to measure changes in mechanical and dimensional properties of the stratum corneum as a result of temperature-induced transformations such as lipid melting and protein conformational changes. The TMA technique is well-known and involves the use of a weighted probe resting on a sample and the measurement of the probe's linear displacement as the sample is heated at a programmed rate. The procedure and some test results are described, for example, in an article written by William T. Humphries, M.S. and Richard H. Wildnauer, Ph.D. entitled *Thermomechanical Analysis of Stratum Corneum,* The Journal of Investigative Dermatology, 32–37, 1971.

Another technique utilizes a strain gauge to determine the dimensional changes of a skin sample immersed in a water bath of controlled temperature. *Isometric Contraction of Epidermis and Stratum Corneum with Heating,* Howard P. Baden, M.D. and Ann M. Gifford, The Journal of Investigative Dermatology, 298–303, 1970.

Both of the foregoing technique are limited in their ability to alter various other parameters affecting normal skin (e.g. humidity, temperature, topical agents, etc.) while simultaneously measuring the changes in the viscoelastic properties of the samples being tested. An example of a method and apparatus which is used for determining the viscoelastic properties of excised skin, and which overcomes some of the deficiencies of the foregoing techniques is described in an article entitled *Viscoelastic Properties of Intact Human Skin: Instrumentation, Hydration Effects and the Contribution of the Statum Corneum,* M. S. Christensen, C. W. Hargens III, S. Nacht, E. H. Gans, The Journal of Investigative Dermatology, 69: 282–286, 1977. The procedure entails the use of an electrodynamometer utilizing a gas suspended armature which oscillates in response to changes in the magnetic field generated by a surrounding coil. The coil is activated in a sinusoidal mode by a function generator, and the displacement of the armature is monitored by a linear variable differential transformer. A stiff wire probe connects the armature to the skin sample and measurements of the skin displacement are made as a function of the force applied to the armature. The time lag between the applied force and the resulting deformation of the skin surface is a characteristic of materials which, like skin, are viscous and not perfectly elastic. One disadvantage of this procedure is that it, like the previously described techniques, does not provide means to vary many of the ambient conditions under which the skin sample is tested. Topical agents may be applied, but the absence of a water bath will cause the sample to dry out over time, thus affecting the repeatability and reliability of any measurements being made. It should also be noted that the viscoelastic properties of the skin will be affected by the ambient temperature as well and this procedure does not provide means to vary this parameter.

In addition to skin's viscoelasticity characteristics, another parameter of interest is its transepidermal water loss under varying conditions. Known instrumentation for measuring this characteristic operates in vivo utilizing two spaced thin film capacitors placed in an enclosure over a portion of a (human) subject's skin. The humidity gradient sensed by the two capacitors is calculated as necessary. An example of an instrument capable of performing this function in vivo is the Evaporimeter EP 1C or 1D, manufactured by ServoMed, Riddersviksvä gen 107, Stockholm-Hässelby, Sweden. However, no instrumentation is known for measuring transepidermal water loss in vitro and under selectively variable ambient conditions.

While in vitro measurements of skin flexibility and other characteristics such as transepidermal water loss may be more accurate than in vivo measurements, it must be noted that, as explained above, prior art in vitro procedures suffer from the inability to adequately vary the temperature and humidity (and other) conditions to which living tissue is normally subjected. Data thus obtained with these previously known techniques is, therefore, of limited usefulness. There is, therefore, a need for an in vitro procedure and apparatus which can overcome the deficiencies of the prior art by enabling simulated in vivo measurements under conditions approximately those of living tissue.

It is accordingly an object of this invention to provide a method and apparatus capable of making accurate, simulated in vivo measurements of the viscoelastic properties of skin.

It is another object of this invention to provide a method and apparatus for determining the viscoelastic properties of skin samples in vitro while enabling control of ambient temperature and humidity to simulate in vivo conditions.

It is a further object of this invention to provide a method and apparatus for determining the viscoelastic properties of skin samples vitro under varying ambient conditions and varying topical agents.

It is still another object of this invention to provide a method and apparatus for determining the transedpidremal water loss of skin samples in vitro under varying ambient conditions and varying topical agents.

SUMMARY OF THE INVENTION

These and other objects of the invention are achieved by the preferred embodiment which is, in an apparatus for measuring the viscoelastic properties of a skin sample, the apparatus having a proble means for applying a force to the skin sample and a measuring means for measuring the displacement of the skin sample in response to said force, the improvement comprising: a platform for peripherally supporting the skin sample over a chamber containing liquid such that the top surface of the liquid is in contact with the bottom of the skin sample; and temperature regulating means for controlling the temperature of said liquid. The preferred embodiment may also include means to apply various topical agents to the sample while varying ambient temperature and humidity.

In another embodiment of this invention the platform is utilized with an air chamber over the skin sample and a humidity testing apparatus, the temperature and humidity of the air being controllable to determine transepidermal water loss.

BRIEF DESCRIPTION OF THE DRAWINGS

FIG. 1 is a diagrammatic perspective view of a platform (for supporting an excised skin sample during in vitro measurements) and associated test instrumentation.

FIG. 2 is a plan view of FIG. 1.

FIG. 3 is a cross-sectional view of FIG. 2 taken along lines 3—3.

DESCRIPTION OF THE PREFERRED EMBODIMENT

Figure 4:
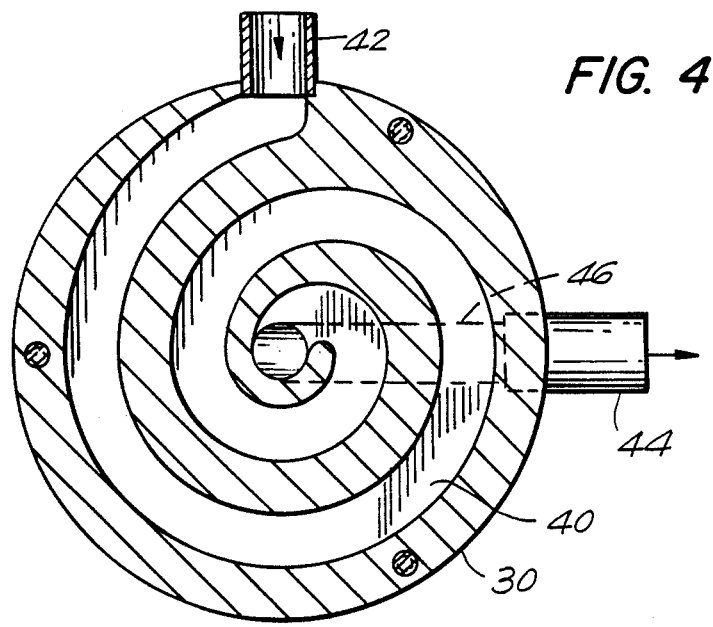
FIG. 4 is a cross-sectional view of FIG. 3 taken along lines 4—4.

In FIG. 1 there is shown a perspective view of the supporting platform 10 constructed in accordance with the principles of this invention. Supporting platform 10 is intended for use with test instrumentation 12 which may include, for example, a gas-bearing electrohynamometer having a probe 14. Other associated equipment such as a function generator, oscilloscope, etc. is not shown. The electrodynamometer is connected to this other equipment in a manner that will be understood by those skilled in the art. Probe 14 is bent at its distal end 15 and bonded by suitable bonding material to a plastic interface disc 16 which is itself suitably bonded to the top surface of a skin sample 17 which is retained within supporting platform 10. Sample 17 may be the stratum corneum or may be any desired portion of the skin.

Figure 5:
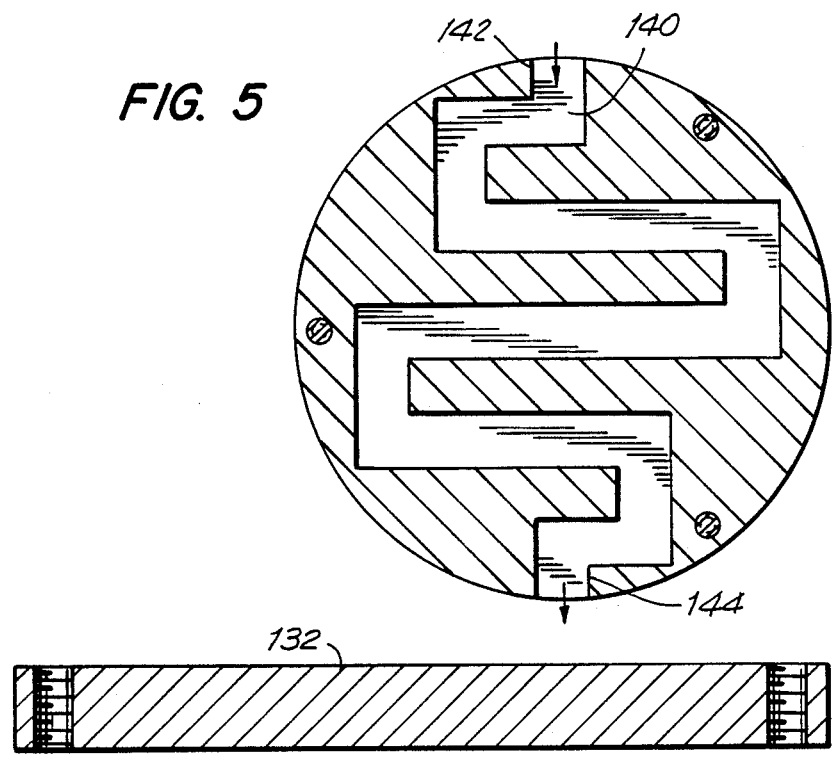
FIG. 5 is an alternative embodiment of FIG. 4.

Platform 10 comprises three axially aligned cylindrical plates 30, 32 and 34. Bottom plate 30 is, in the preferred embodiment, a solid block of aluminum having milled therein a water passage 40 in a predetermined configuration. As best seen in FIG. 4, water passage 40 is a spiral channel having a water inlet 42 and a water outlet 44. As best seen in FIG. 3, a connecting tube or bore 46 joins the center of the spiral channel to the outlet pipe 44. An alternate water channel configuration 140 having diametrically opposed water inlet and outlet channels 142 and 144, respectively, is shown in FIG. 5 and does not require a connecting bore 46. It will be understood by those skilled in the art that bottom plate 30 should be relatively massive in order to enhance temperature stability of platform 10.

The top of water channel 40 is covered by a stainless steel middle plate 32 to produce a sealed water channel within platform 10 through which water, maintained at a predetermined temperature, may be circulated in the direction of the arrows by a temperature regulating apparatus (not shown).

Middle plate 32 is provided with a well 50 which, in the operation of the apparatus, may be filled with a predetermined liquid or may be left empty. The liquid helps to simulate in vivo conditions by maintaining moisture in the sample. It is preferably to have well 50 centrally disposed within middle plate 32 in order to enhance the temperature stability of any liquid contents of the well. Any uneven distribution of the thermal mass surrounding the well would result in non-uniform temperature distribution of the liquid in the well. Well 50 is also used in measuring transedpidermal water loss as more fully described below with respect to FIGS. 7 and 8.

Figure 6:
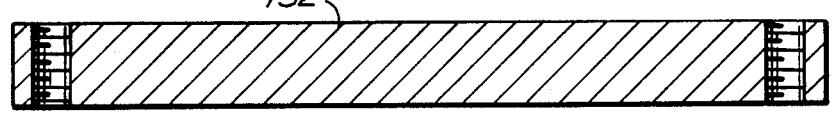
FIG. 6 is an elevational view of an alternate embodiment of a component of the invention.

For those experiments where it is not desired to expose the skin sample to a liquid, alternative middle plate 132 is shown in FIG. 6 could be used. This would still enable temperature control of the sample.

A top plate 34 is placed over well 50 and all three portions of the heating platform 10 are secured together by screws 36 and wing nuts 37, or the like. The sample of skin 17 to be tested is, before assembly, interposed between middle plate 32 and top plate34. Top plate 34 is provided with an axially aligned annular lip 52 surrounding and at the bottom of a central bore 54. The bottom surface 56 of lip 52 presses the periphery of skin sample 17 against the top of middle plate 32 adjacent the well 50. This construction minimizes shear stress to the skin surface during assembly of the apparatus and enables the sample to be maintained under constant tension during the course of any particular experiment. Top plate 34 is provided with a bore 58 through which probe 14 may pass in order to be attached to the sample. Additional bores or auxiliary tubes (not shown) may also be provided in plate 34 to facilitate filling (and evacuating) bore 54 with desired fluids or applying selected topical solutions to the skin surface without disturbing the experimental set-up. Auxiliary equipment may also be provided above bore 54 to change the temperature and humidity of air directly over the sample as desired.

Various measurements of the viscoelastic properties of the sample may be made with the apparatus shown. For example, while the temperature of middle plate 32 is held constant the oscillations of the probe tip 15 could be varied in a predetermined manner to determine the reaction of the sample. As another example, the vibrations of the tip 15 could be held constant while the temperature is varied. In all situations, various topical agents could be applied to the skin sample through bore 54 to determine their effect on the viscoelastic properties of the sample under varying conditions. If desired, the entire top surface of the sample could be covered by filling bore 54 with a desired liquid (e.g. water to eliminate hydration). The entire apparatus could be encased in insulating material (not shown) or a temperature and humidity controlled housing (not shown) and mounted on vibration isolation devices (not shown) to further enhance control of ambient parameters during use.

Figure 7:
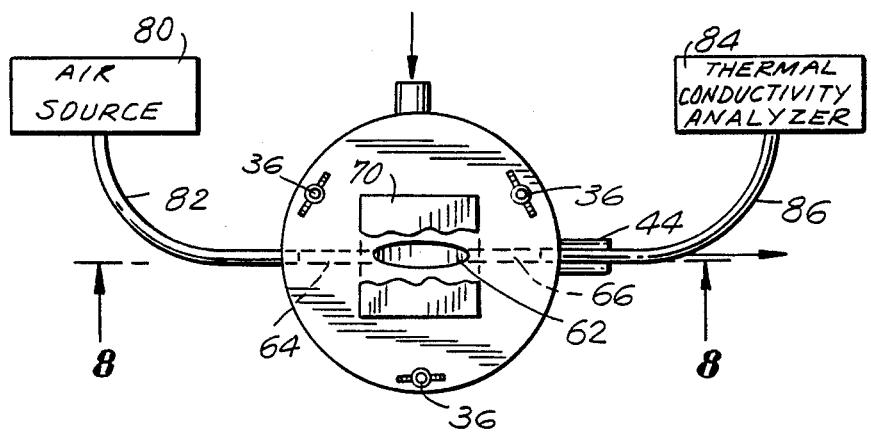
FIG. 7 is a diagrammatic plan view of another embodiment of the invention.
Figure 8:
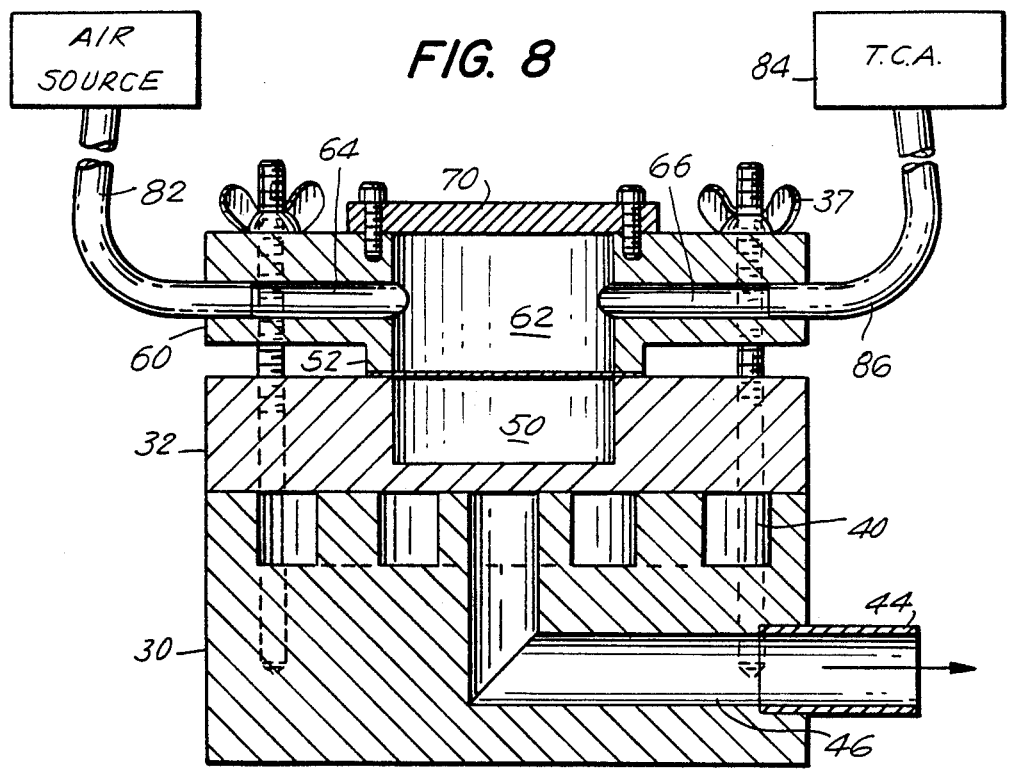
FIG. 8 is a view of FIG. 7 taken along the line 8—8.

The embodiment of the invention shown in FIGS. 7 and 8 is similar to the previously described embodiment. However, the top plate configuration has been changed to that of plate 60 which has a generally rectangular chamber centrally located to fit over a skin sample similarly to the central bore 54 of top plate 34. Chamber 62 has an inlet bore 64 and an outlet bore 66 for conducting air into and out of chamber 62. Cover 70 is used to enclose chamber 62 during the measurement of transepidermal water loss, although the cover may be easily removed to enable the application of various topical agents to the sample without disturbing the sample itself. An air source pump 80 is connected via tube 82 to inlet bore 64 and a thermal conductivity analyzer 84 is connected to outlet bore 66 via tube 86. Air flowing from source 80 through chamber 62 will pick up a certain amount of moisture because of the transmission of the liquid in well 50 through the skin sample. The amount of moisture in the air above this sample will be determined by the thermal conductivity analyzer 84 or some other suitable moisture sensing apparatus in order to determine the transepidermal water loss through the skin sample.

It will be understood by those skilled in the art that numerous other modifications and improvements may be made to the preferred embodiment of the invention disclosed herein without departing from the spirit and scope thereof.

What is claimed is :

1. In a method of measuring a characteristic property of a sample of skin comprising the step of determining a predetermined parameter associated with said characteristic, the improvement comprising the steps of:
    (a) supporting the skin sample over a chamber having an open top and containing a predetermined liquid, the liquid being contiguous with one side of the skin sample, and
    (b) maintaining the liquid at a predetermined temperature for a predetermined time.

2. A method according to claim 1 wherein the skin sample is peripherally supported over said open top of said chamber.

3. A method according to claim 1 further comprising the step of:
    (c) measuring the amount of said liquid passing through said skin sample in a predetermined time period.

4. A method according to claim 1 further comprising the steps of:
    (c) attaching a displacement-measuring probe means to said skin sample,
    (d) activating said probe means to displace said skin sample in a predetermined manner,
    (e) measuring the displacement of said skin sample.

5. In an apparatus for supporting a skin sample during the measurement of predetermined characteristics of said skin sample, the improvement comprising:
    a platform for supporting the skin sample, said platform having a top surface with a chamber therein having an open top;
    a predetermined liquid in said chamber, the top surface of the liquid being in contact with the bottom of the skin sample; and
    temperature regulating means for controlling the temperature of said liquid.

6. In an apparatus according to claim 5 wherein said temperature regulating means comprises:
    circulating means for circulating a temperature maintaining fluid through an object to be heated; and
    heating and controlling means for heating the fluid being circulated through said object and for controlling the temperature thereof, the improvement further comprising:
    base means secured to the bottom of said platform, said base means provided with a fluid channel for enabling the flow of said temperature maintaining fluid therethrough.

7. In an apparatus according to claim 5 the improvement further comprising:
    an annular cover secured to said platform, said cover having at least one aperture therethrough enabling access to the top surface of said skin sample through said aperture.

8. In an apparatus according to claim 7 the improvement further comprising:
    an annular lip on the bottom of said cover, said lip adjacent the bottom of said aperture and adapted to peripherally press said skin sample against a cooperating peripheral surface area around the open top of said chamber.

9. In a method of measuring a characteristic property of a sample of skin comprising the step of determining a predetermined parameter associated with said characteristic, the improvement comprising the steps of:
    (a) supporting the skin sample over a chamber having an open top and containing a predetermined liquid, the liquid being contiguous with one side of the skin sample,
    (b) maintaining the liquid at a predetermined temperature for a predetermined time,
    (c) attaching a displacement-measuring probe means to said skin sample,
    (d) activating said probe means to displace said skin sample in a predetermined manner, and
    (e) measuring the displacement of said skin sample.

10. A method according to claim 9 further comprising the step of determining the temporal relationship between the displacement force applied to said skin sample and the actual displacement thereof as a function of the temperature of said liquid.

11. In an apparatus for supporting a skin sample during the measurement of predetermined characteristics of said skin sample, the improvement comprising:
    a platform for supporting the skin sample, said platform having a top surface with a chamber therein having an open top,
    a predetermined liquid in said chamber, the top surface of the liquid being in contact with the bottom of the skin sample,
    temperature regulating means for controlling the temperature of said liquid, an annular cover secured to said platform, said cover having at least one aperture therethrough enabling access to the top surface of said skin sample through said aperture, and an annular lip on the bottom of said cover, said lip adjacent the bottom of said aperture and adapted to peripherally press said skin sample against a cooperating peripheral surface area around the open top of said chamber.

12. In an apparatus according to claim 11 the improvement further comprising:

a cover means for sealing each of each apertures, an inlet access means for enabling fluid to flow into the space between said cover means and said sample, an outlet access means for enabling fluid to flow out of said space, a fluid source means for causing fluid to flow into said inlet access means, and an analyzing means for receiving fluid from said outlet access means and for determining a predetermined characteristic thereof.

13. An apparatus according to claim 12 wherein said fluid is air; said liquid is water and said predetermined characteristic is the amount of water vapor in the air.

* * * * *